(12) United States Patent
Weiler et al.

(10) Patent No.: US 10,213,331 B1
(45) Date of Patent: Feb. 26, 2019

(54) POSTURE ENHANCEMENT DEVICE

(71) Applicants: Wolfgang Weiler, Oneida, WI (US);
Carlyn Weiler, Oneida, WI (US)

(72) Inventors: Wolfgang Weiler, Oneida, WI (US);
Carlyn Weiler, Oneida, WI (US)

( * ) Notice: Subject to any disclaimer, the term of this patent is extended or adjusted under 35 U.S.C. 154(b) by 799 days.

(21) Appl. No.: 13/907,369

(22) Filed: May 31, 2013

(51) Int. Cl.
*A61F 5/02* (2006.01)

(52) U.S. Cl.
CPC ...................... *A61F 5/02* (2013.01)

(58) Field of Classification Search
CPC .. A61F 5/01; A61F 5/37; A61F 5/3746; A61F 5/02–5/042; A61F 5/058–5/05808; A61F 5/3715–5/3753; A41D 13/1245; A41D 13/1236; A63B 69/0057–69/0059
See application file for complete search history.

(56) References Cited

U.S. PATENT DOCUMENTS

| | | |
|---|---|---|
| 30,601 A | 11/1860 | Wright |
| 114,615 A | 5/1871 | Smitley |
| 245,524 A | 8/1881 | Lubin |
| 363,538 A | 5/1887 | Penny |
| 443,764 A | 12/1890 | Hilliard |
| 807,908 A | 12/1905 | Bradstreet |
| 1,301,276 A | 4/1919 | Kroetz |
| 1,371,690 A | 3/1921 | Kelly |
| 1,581,791 A | 4/1926 | Davison |
| 1,587,716 A | 6/1926 | Fritsch |
| 2,097,376 A | 10/1937 | Marshman |
| 2,224,103 A | 12/1940 | Nilson |
| 2,723,664 A | 11/1955 | Davis |
| 3,141,456 A | 7/1964 | Meek |
| 3,162,442 A | 12/1964 | Karlik |
| 3,194,234 A | 7/1965 | Duckman et al. |
| 3,277,889 A | 10/1966 | Palmer |
| 3,292,616 A | 12/1966 | Freeman |
| 3,295,517 A | 1/1967 | Stevens |
| 3,315,671 A | 4/1967 | Creelman |
| 3,338,236 A | 8/1967 | McLeod, Jr. |
| 3,382,868 A | 5/1968 | Steifel |
| 3,523,859 A | 8/1970 | Komp |
| 3,620,211 A | 11/1971 | Goodell |
| 3,856,004 A | 12/1974 | Cox |
| 3,897,776 A | 8/1975 | Gaylord, Jr. |
| 4,007,733 A | 2/1977 | Celeste et al. |

(Continued)

*Primary Examiner* — Alireza Nia
*Assistant Examiner* — Michelle Lee
(74) *Attorney, Agent, or Firm* — Lempia Summerfield Katz LLC (57) ABSTRACT

A wearable posture enhancement device triggers muscles in the body to act to enhance posture of the body. The posture enhancement device is not a brace and does not apply any forces to the body sufficient to force the body to move to any position or hold any position. The posture enhancement device includes a torso strap, arm straps, and a posture signaling panel. The torso strap is configured to hold the posture enhancement device to a human body at a first pressure level. The posture signaling panel extends from a front of the torso strap to a back of the torso strap. The posture signaling panel is configured to provide a second pressure level to the human body, and the second pressure level signals muscles to correct posture of the human body. The second pressure level is less than the first pressure level.

13 Claims, 5 Drawing Sheets

(56) References Cited

U.S. PATENT DOCUMENTS

| | | |
|---|---|---|
| 4,055,168 A | 10/1977 | Miller et al. |
| 4,080,962 A | 3/1978 | Berkeley |
| 4,226,231 A | 10/1980 | Andersen |
| 4,325,363 A | 4/1982 | Berkeley |
| 4,438,763 A | 3/1984 | Zablen |
| 4,446,858 A | 5/1984 | Verter |
| 4,480,637 A | 11/1984 | Florek |
| 4,526,166 A | 7/1985 | Silber |
| 4,594,999 A | 6/1986 | Nesbitt |
| 4,598,703 A | 7/1986 | Lindemann |
| 4,750,480 A | 6/1988 | Jenness |
| 4,785,803 A | 11/1988 | Benckhuijsen |
| 4,995,383 A | 2/1991 | Andersson |
| 5,007,413 A | 4/1991 | Aalvik Thune |
| 5,018,513 A | 5/1991 | Charles |
| 5,040,524 A | 8/1991 | Votel et al. |
| 5,086,757 A | 2/1992 | Lestini |
| 5,116,306 A | 5/1992 | Zander |
| 5,120,288 A | 6/1992 | Sinaki |
| 5,135,470 A * | 8/1992 | Reeves ............... 602/19 |
| 5,179,942 A | 1/1993 | Drulias et al. |
| 5,199,940 A | 4/1993 | Morris et al. |
| 5,203,763 A | 4/1993 | Lajiness-O'Neill |
| 5,226,874 A | 7/1993 | Heinz et al. |
| 5,360,391 A | 11/1994 | Johnson |
| 5,405,313 A | 4/1995 | Albin |
| 5,435,563 A | 7/1995 | Salvatore |
| 5,613,893 A * | 3/1997 | Zagame ............... 450/155 |
| 5,860,896 A | 1/1999 | Mann |
| 5,868,691 A | 2/1999 | Vishnevsky |
| 6,387,067 B1 | 5/2002 | Hebert |
| 6,440,094 B1 * | 8/2002 | Maas ............... 602/5 |
| 6,709,411 B1 * | 3/2004 | Olinger ............... 602/4 |
| D499,806 S | 12/2004 | Machin et al. |
| 6,991,611 B2 | 1/2006 | Rhee |
| 7,744,511 B2 | 6/2010 | Grigoriev et al. |
| 7,842,000 B2 * | 11/2010 | Lai et al. ............... 602/19 |
| 7,902,420 B2 | 3/2011 | Kase |
| 8,047,893 B2 * | 11/2011 | Fenske ............... A41C 3/005 450/85 |
| 2005/0070830 A1 | 3/2005 | Schultz |
| 2008/0208089 A1 | 8/2008 | Newkirk et al. |
| 2009/0062704 A1 | 3/2009 | Brown et al. |
| 2009/0171259 A1 * | 7/2009 | Soerensen et al. ............... 602/67 |
| 2010/0050313 A1 | 3/2010 | Shackelford, Jr. |
| 2010/0312160 A1 | 12/2010 | Creighton et al. |
| 2012/0316483 A1 * | 12/2012 | Waeger ............... 602/19 |
| 2014/0058311 A1 * | 2/2014 | Higgins ............... A61F 13/08 602/63 |

* cited by examiner

POSTURE ENHANCEMENT DEVICE

FIELD

The following disclosure relates to a wearable posture enhancement device, or more particularly, to a wearable posture enhancement device configured to provide a reminding force to a human body.

BACKGROUND

Proper posture leads to good health and appearance. Slouching decreases the size of the cavity for the organs of the human body. Proper posture increases the size of the cavity. The added space in the organ cavity allows the lungs to expand fully to receive more air and allows the heart and circulatory system to pump more blood with less effort. Pressure on other organs, such as the intestines, stomach, kidneys, liver, pancreas, is also decreased. In addition, proper posture also alleviates common problems such as back or neck pain, headaches, and fatigue.

Techniques for correcting posture without external aids often involve stretching, exercise, and mental awareness for holding the body in alignment. Conventional external aids focus on pulling the shoulders backwards to force proper posture.

SUMMARY

In one embodiment, a wearable posture enhancement device triggers muscles in the body to act to enhance posture of the body. The posture enhancement device is not a brace and does not apply any forces to the body sufficient to force the body to move to any position or hold any position. The posture enhancement device includes a torso strap, arm straps, and a posture signaling panel. The torso strap is configured to hold the posture enhancement device to a human body at a first pressure level. The posture signaling panel extends from a front of the torso strap to a back of the torso strap. The posture signaling panel is configured to provide a second pressure level to the human body, and the second pressure level signals muscles to correct posture of the human body. The second pressure level is less than the first pressure level.

BRIEF DESCRIPTION OF THE DRAWINGS

Exemplary embodiments of the present invention are described herein with reference to the following drawings.

DETAILED DESCRIPTION

The disclosed embodiments relate to a posture device, a method for making the posture device, and a method for using the posture device. The posture device is not a brace or a support. The posture device is a suggestive device. The posture device provides light pressure on one or more selected points on the human body to remind or encourage the human body to improve posture. The posture device gives the feeling of widening through the collarbones and chest, allowing the collarbones to lift, which centers the head and neck muscles over the correct axis. The posture device also creates a release in the shoulder joint, allowing the arm muscles to relax and the humerus bone to hang freely from the shoulder joint. The posture device encourages a centered alignment of the body, which is defined as the ear, shoulder, and hip all being in substantially a straight line. Substantially a straight line may mean within an angle of 10 degrees.

Kinaesthesia is the sense of body motion or the conscious awareness of body position and movement. The sensation by which the body positions itself based on weight, muscle tension, and movement is governed by kinaethesia. Many movements are unconscious as the sensory system respond to light sensation of pressure. The following embodiments describe posture enhancement devices that are worn on the body and are configured to apply light pressure to the body and trigger the body to respond by correcting posture.

The shoulder girdle area includes the clavicles, which is elongated, and scapulae, which are triangular shaped. The shoulder girdle is coupled to the thoracic vertebrae and has a direct effect on the posture of the body. The shoulder girdle is also coupled to the rib cage and the arms. The movement of the arms directly affects the position and orientation of the shoulder girdle, impacting the posture of the body. The posture enhancement device is configured to apply small forces to the shoulder girdle to equalize the shoulder girdle and improve the posture of the body and thoracic vertebrae.

Neck injuries, working conditions, degenerative diseases or other external forces may cause permanent damage to the body, resulting in poor posture. The deterioration of posture over time may be referred to as kyphosis. Some minor instances of kyphosis may be prevented or lessened through use of the posture enhancement device. The posture enhancement device is configured to apply light forces to the body to remind the body to correct posture, which can reverse some effects of kyphosis.

Figure 1:
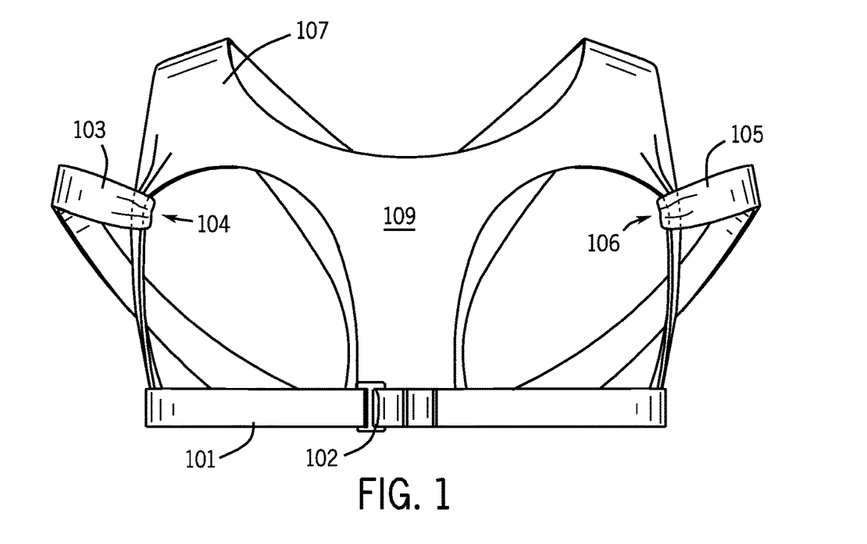
FIG. 1 illustrates a front view of an example posture enhancement device.
Figure 2:
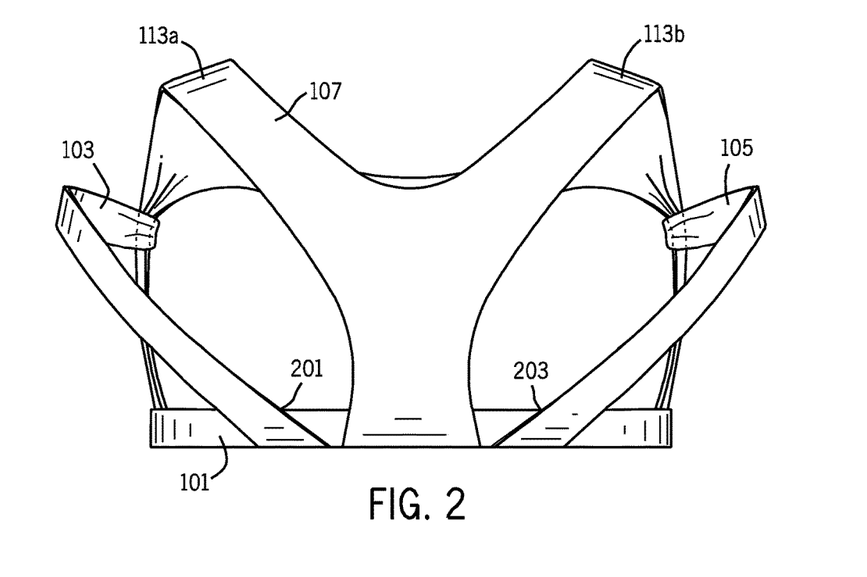
FIG. 2 illustrates a rear view of the example posture enhancement device of FIG. 1.

FIG. 1 illustrates an example posture enhancement device (e.g., posture correction device). The posture enhancement device includes a torso strap 101, a first arm strap 103, a second arm strap 105, and a posture signaling panel 107. FIG. 2 illustrates a rear view of the example posture enhancement device of FIG. 1. FIG. 2 also illustrates a left posterior portion 113a and a right posterior portion 113b of the posture signaling panel 107 and connection 203 of the of the second arm strap 105 to the torso strap 101 and connection 201 of the first arm strap 103 to the torso strap 101.

The torso strap 101 is configured to hold the posture correction device to a human body at a first pressure level via coupling device 102. The coupling device 102 may be a buckle, a snap, a zipper, or other fastening device configured to hold the torso strap 101 to the human body. In one embodiment, the posture enhancement device does not include the coupling device 102. Instead, the torso strap may be or may include, for example, an elastic strap to hold the posture correction device to the body. The first arm strap 103 and the second arm strap 105 are coupled to the torso strap 101. In one embodiment, the first arm strap 103 and/or the second arm strap 105 may not be coupled to the torso strap 101. Instead, the first arm strap 103 and/or the second arm strap 105 may be coupled to different sides of the posture signaling panel 107. In other embodiments, the posture enhancement device may include more or fewer arm straps coupled to the torso strap 101 and/or the posture signaling panel 107 (e.g., four arm straps).

The posture signaling panel 107 extends from a front of the torso strap 101 to back of the torso strap 101. An anterior portion 109 of the posture signaling panel 107 is secured to the torso strap 101. The posture signaling panel 107 is configured to provide a second pressure level to the human body, and the second pressure level signals muscles to correct posture of the human body. The second pressure level is less than the first pressure level.

The second pressure level causes the human body to lift the collarbone, push out the sternum, flatten the shoulder girdle, and/or straighten the thoracic vertebrae. The second pressure level may cause the human body to lengthen, soften, and/or widen the sternum. The posture signaling panel 107 includes the anterior portion and a posterior portion. The posterior portion is aligned with a shoulder blade, and the anterior portion is aligned with a collar bone, such that the posture signaling device signals the human body to center and become aligned. In one embodiment, the anterior portion and the posterior portion of the posture signaling panel 107 are different portions of a single part (e.g., a single piece of material). Alternatively, the anterior portion and the posterior portion are different parts that may, for example, be made of the same material or different materials. The anterior portion and the posterior portion may be secured together with, for example, stitching.

The posture enhancement device does not push or pull the body into place. The posture enhancement device does not include any braces or physically hold any part of the body in place or in any orientation. The second pressure level may be a lifting force under the collar bone. However, the lifting force is very small. The posture enhancement device reminds the muscles of the body of the pathways where the muscles belong but have fallen out of place.

A variety of materials may be used for the posture enhancement device. The materials may be any elastic material comfortable for wearing on the human body. The elasticity of the material may configured to apply a suggestive force to the body. The suggestive force is in a range of 5 to 30 grams per square centimeter. The elasticity of the material may be selected to apply the suggestive force. The suggestive force is less than a force applied to the body by the torso strap 101. The force applied to the body by the torso strap 101 may be at a pressure level greater than 30 grams per square centimeter. In another example, the suggestive force is in the range of 40-100 grams per square centimeter, and the force applied by the torso strap 101 is greater than 100 grams per square centimeter.

An example modulus of elasticity for the material of the posture enhancement device may be in the range of 0 to 4 newtons/m², or more specifically 0.5 to 2 newtons/m². The modulus of elasticity may vary under various types of loading. The types of loading may include tensile loading, bending, and compression. The modulus of elasticity provides a relationship between the amount of displacement of the material of the posture enhancement device and the pressure of force applied to the body by the posture enhancement device.

In one example, the materials for the posture signaling panel 107 are different than the materials for the torso strap 101. The materials for the posture signaling panel 107 may have a different modulus of elasticity that the materials for the torso strap 101. In one example, the modulus of elasticity for the posture signaling panel 107 is in the range of 0.5 to 1.0 newtons/m², and the modulus of elasticity of the torso strap 101 is in the range of 1.0 to 2.0 newtons/m².

The posture enhancement device may include a breathable material. The breathable material may include a breathable pattern of material including fibers in a predetermined pattern. The pattern may be a checkerboard pattern, a twill pattern, or a cross-twill pattern. The material for the posture enhancement device may be fiber based. The fibers may be natural fibers or synthetic fibers. The fibers may have a great amount of stretch and a low modulus of elasticity. Example fibers include spandex, elastrane, lycra, a polyurethane-polyurea copolymer, or another synthetic fiber. An example synthetic fiber may be produced with a macroglycol and a diisocyanate monomer. The process of forming the fiber may include melt extrusion, reaction spinning, solution dry spinning, solution wet spinning, or a combination thereof.

The material of the posture enhancement device may have a low coefficient of friction. Example coefficients of friction are in the range of 0.2 to 0.4. In one example, the coefficient of friction for the posture signaling panel 107 is less than the coefficient of friction for the torso strap 101. An example coefficient of friction for the posture signaling panel 107 may be 0.25, and an example for the coefficient of friction for the torso strap 101 may be 0.35.

Figure 3:
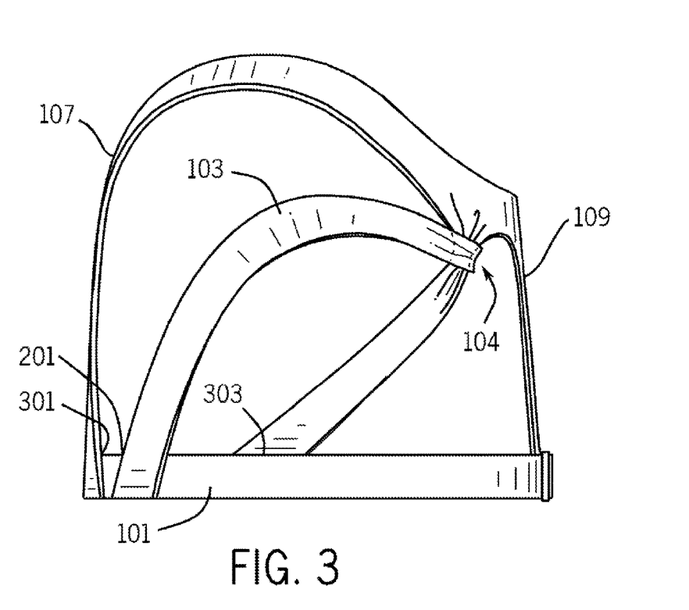
FIG. 3 illustrates a side view of the example posture enhancement device of FIG. 1.

FIG. 3 illustrates a side view of the example posture enhancement device of FIG. 1. The first arm strap 103 may be slidably coupled to the posture signaling panel 107. The connection point 104 may adjust so that the first arm strap 103 adjusts to various angles relative to the torso strap 101 and/or the posture signaling panel 107. The adjustable connection points 104 and 106 ensure that a balance force is applied by the first arm strap 103 to the posture signaling panel 107. The balanced force creates a release in the shoulder joint allowing the arm muscles to relax and the humerus bone to hang freely from the shoulder joint. The adjustable connection point 104 may be omitted, and the first arm strap 103 may be fixedly connected to the posture signaling panel 107. The torso strap 101, the first arm strap 103, the second arm strap 105, and the posture signaling panel 107 may be coupled together, for example, in the manner described above in any number of ways including, for example, with stitching, with an adhesive, with other connectors, or a combination thereof.

FIG. 3 also illustrates a connection point 301 between the torso strap 101 and the back of the posture signaling panel 107 and a connection point 303 between the torso strap 101 and the front of the posture signaling panel 107. The connection points 301 and 303 may be adjustable or fixed.

Figure 4:
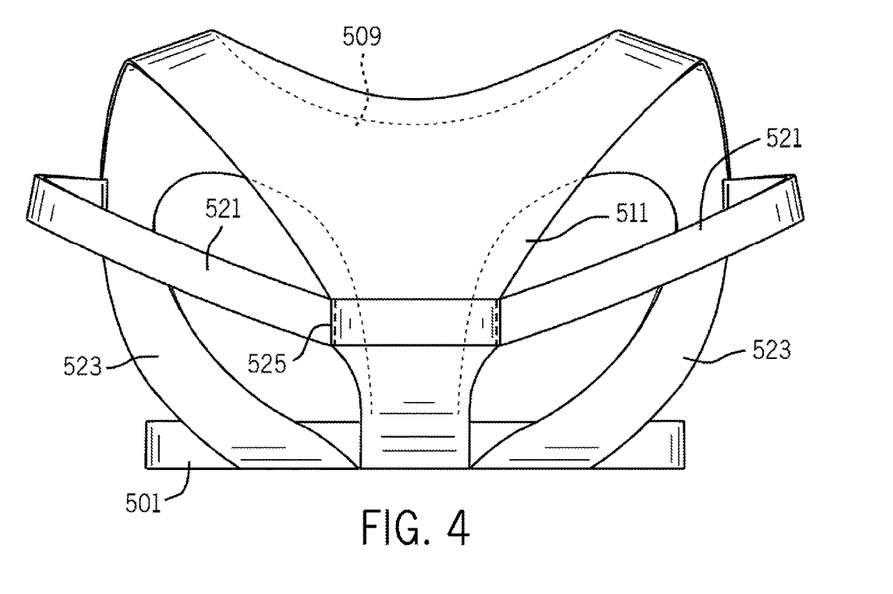
FIG. 4 illustrates a second embodiment of a posture enhancement device.

FIG. 4 illustrates a second embodiment of a posture enhancement device. The posture enhancement device of FIG. 4 includes a securing strap 501, a back panel 511, a chest panel 509, and a single arm strap 521. The back panel 511 is a posterior portion of the posture signaling panel, and the chest panel 509 is an anterior portion of the posture signaling panel. Side straps 523 extend from the chest panel 509 to the rear of the securing strap 501. The arm strap 521 adjustably connects to the back panel 511 through an opening 525 in the back panel 511. The opening 525 allows the arms to balance. The opening 525 may be lined with a rigid material such as plastic.

A distance from the opening 525 on the back panel 511 to the securing strap 501 may be selected to adjust the amount of the pressure placed on the human body to signal muscles to correct posture of the human body. The distance from the opening 525 on the back panel 511 to the securing strap 501 may be ⅓ of the total distance to the top of the posture enhancement device, or the distance may be selected from between 5 and 10 centimeters from the securing strap 501.

Figure 5:
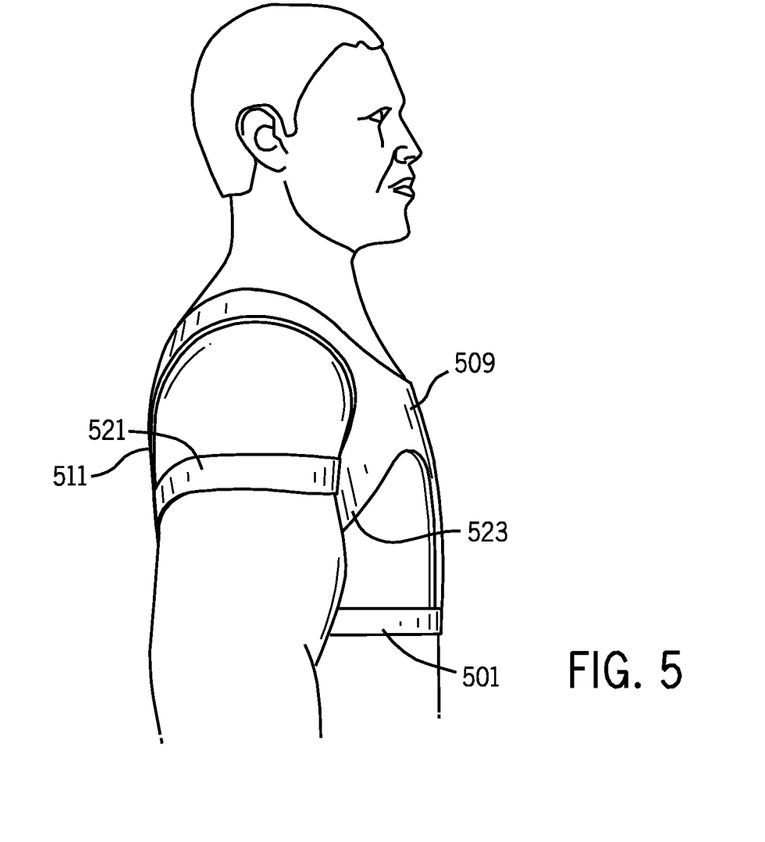
FIG. 5 illustrates a side view of the second embodiment of the posture enhancement device.

FIG. 5 illustrates a side view of the second embodiment of the posture enhancement device as worn by the human body. The posture signaling device stimulates intercostal muscles of the human body to enhance breathing. The intercostal muscles are stabilizing muscles such as the serratus anterior, the lower trapezius, the deep neck flexors, and transverse abdominals. The stabilizing muscles maintain posture or hold the body in position as a platform so that other muscles hold the body and cause the body to move. The stabilizing muscle fibers perform a minimal contraction over an extended period of time and work against gravity. The stabilizing muscles may become weak over time when underutilized. People with poor postural alignment or inactive lifestyle have insufficient tone in these muscles.

The upper fibers of the trapezius are frequently over solicited in work (e.g. sitting at a computer or driving a car) involving prolonged suspension of the arms, with resulting symptoms of sore neck, muscle stiffness, muscle spasm, headache, or other ailments. Many daily postures involve seated positions where the upper trapezius, the levator scapulae and the rhomboids are constantly being contracted (elevated), causing upward rotation of the scapulae and elevation of the clavicle (shoulder girdle). Inefficient breathing patterns may be caused by vertical shoulder girdle movement due to muscle imbalance, tight scalenes, supras-capular muscles and reduced activation of serratus anterior.

The posture signaling device triggers the primary stabilizing muscles to engage, the elevation muscles to relax and the middle fibers of the trapezius to act in synergy with serratus anterior to stabilize the scapulae. When the scapulae are stabilized the inferior fibers of the serratus, the pectoralis minor, the sternocloidomastoid and the levator scapulae assist in inspiration and breathing. The serratus anterior working together with the intercostal muscles assists in inspiration and breathing to laterally expand the rib cage. Therefore, the posture signaling device stimulates one or more of these muscle groups to create a correct breathing pattern. The correct breathing pattern increases awareness, thoracic control and use of the lower ribs, which may be referred to as trunk control. The correct breathing pattern also enhances the connection between the pelvic floor and the diaphragm, which may be referred to as core control.

Figure 6:
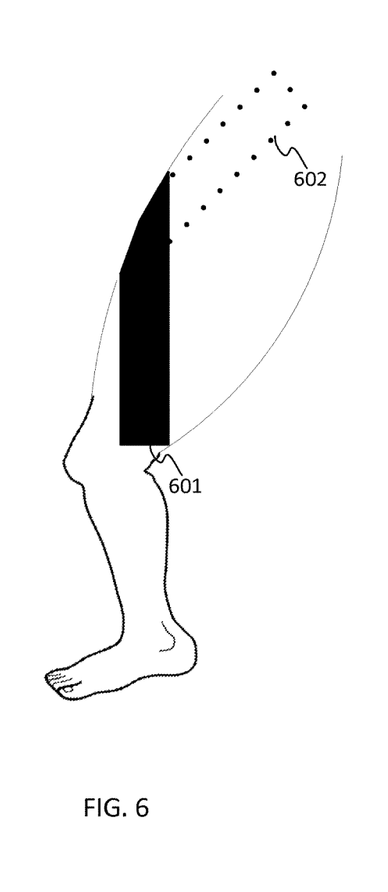
FIG. 6 illustrates an example reminder device.

FIG. 6 illustrates an example reminder device 601. The reminder device 601 is shaped to be worn on the upper leg muscles (e.g., biceps femoris) in order to remind the upper leg muscles to stay aligned with the knee. The reminder device 601 extends from the inside of the knee (e.g., at the sartorius insertion) and lifts up across the middle region of the thigh and ends near the medial gluteus, as shown by the dotted line portion 602. The reminder device 601 simulates a feeling of wrapping the legs. The reminder device 601 is configured to engage the quadriceps and sartorius muscles to balance the thigh muscles allowing the hamstrings to elongate. The reminder device 601 helps to prevent tight hamstrings and locked out knees. These effects help the muscles lift the body away from the direction of gravity, which creates balance in the lower body and encourages the pelvis to sit correctly on the legs. In a balanced lower body, the hip flexors act as stabilizers rather than support muscles, which may occur as a result of poor posture.

Figure 7:
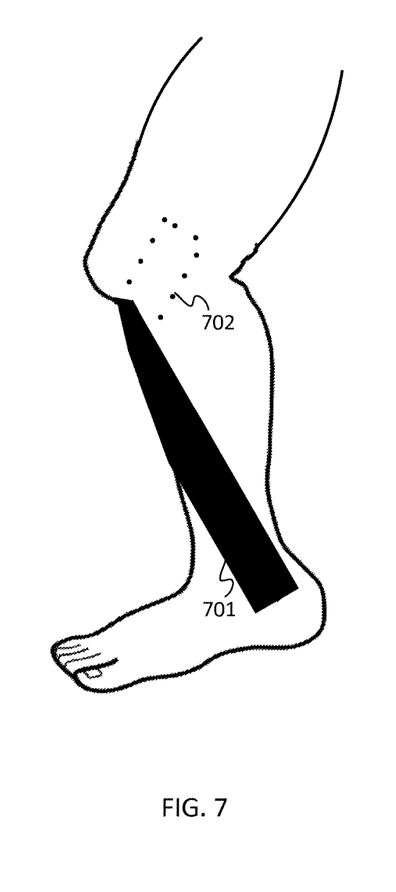
FIG. 7 illustrates another example reminder device.

FIG. 7 illustrates another example reminder device 701. The reminder device 701 is shaped to be worn on the lower leg muscles (e.g., peroneus) to remind the lower leg muscles to stay aligned with the knee and ankle. The reminder device 701 extends from a location near the arch of the foot, crosses over the front of the shin, and ends outside of the knee (e.g., at the origin of the tibialis anterior) shown by dotted lines 702. The reminder device 701 triggers the anterior and posterior muscles of the lower leg to lift the arch of the foot. The reminder device 701 helps to prevent feet that fall in the arch and feet that roll outward.

Figure 8:
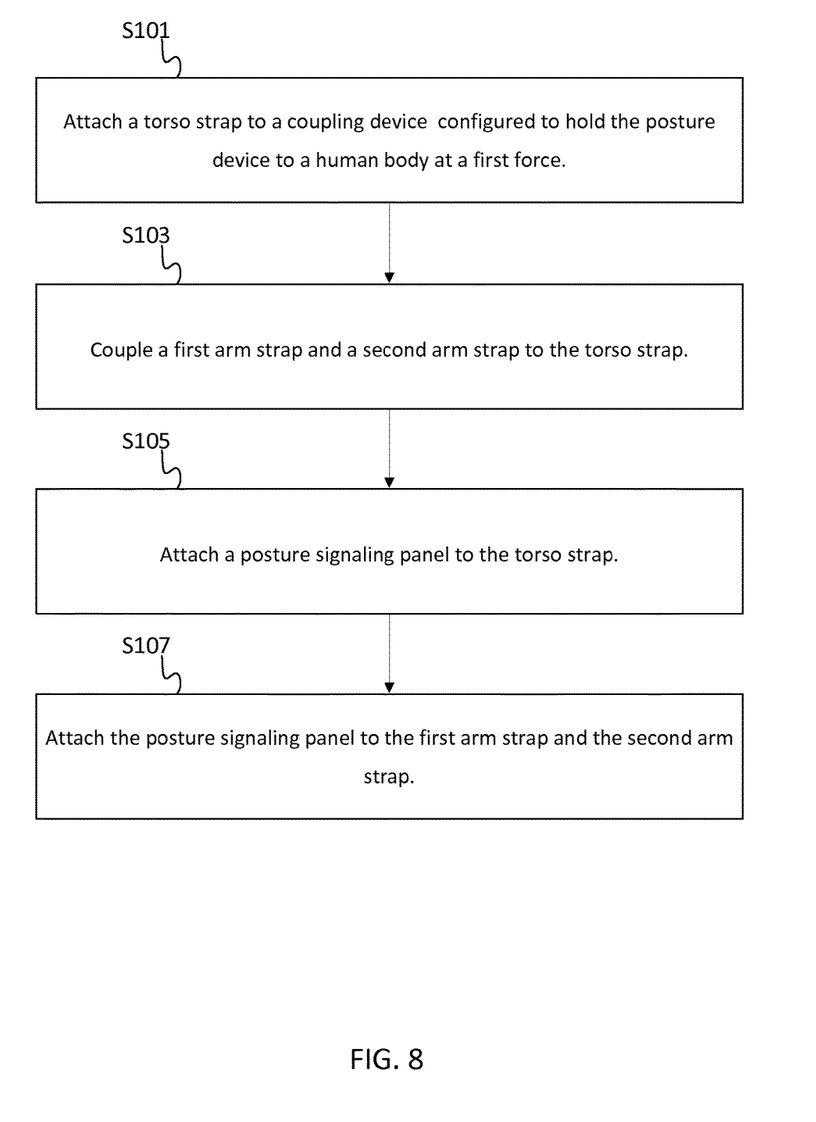
FIG. 8 is an example flow chart for making the posture enhancement device.

FIG. 8 is an example flow chart for making the posture enhancement device. The posture enhancement device may be made manually by hand or by machine. The posture enhancement device may be made by sewing or otherwise coupling the various components. At act S101, a torso strap is attached to a coupling device configured to hold the posture device to a human body at a first force. The coupling device may be a buckle or another fastener. The coupling may be adjustable.

At act S103, a first arm strap and a second arm strap are coupled to the torso strap. At act S105, a posture signaling panel is attached to the torso strap. The posture signaling panel is configured to apply a light suggestive force to induce collar bones to lift and induce the shoulder joint to release, the vertebrae to straighten, and the head to be centered over the body. The light suggestive force may be substantially equivalent to the weight of the posture enhancement device. The light suggestive force may be equivalent to an elastic force dependent on the material for the posture enhancement device. The light suggestive force may be any value between 1 to 2 pounds per square inch. An example light suggestive force ranges from 1.15 pounds per square inch at one portion of the posture signaling panel to 1.50 pounds per square inch at another portion of the posture signaling panel.

At act S107, the posture signaling panel is attached to the first arm strap and the second arm strap. The suggestive force is a second force, which is different that the force of the torso strap, to correct posture of the human body.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, are apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

We claim:

1. A posture enhancement device comprising:
   a torso strap configured to hold the posture enhancement device to a human body at a first pressure level;
   a posture signaling panel including an anterior portion, a posterior portion and first and second side portions, wherein the anterior portion of the posture panel extends from a front of the torso strap to a back of the torso strap, wherein the posture signaling panel is configured to provide a second pressure level to the human body to signal muscles to correct posture of the human body, wherein the second pressure level is less than the first pressure level; and
   a first arm strap with a first end coupled directly to the torso strap and a second end coupled directly to the first side portion of the posture signaling panel and a second arm strap with a first end coupled directly to the torso strap and second end coupled directly to the second side portion of the posture signaling panel, wherein the first arm strap is configured to extend around a first arm of the human body and the second arm strap is configured to extend around a second arm of the human body;
   wherein the second end of the first arm strap and the second end of the second arm strap are each configured to apply a force to the posture signaling panel which is configured to apply a suggestive force aligned with a collar bone of the human body, and wherein the suggestive force aligned with the collar bone is in a range of 5 to 30 grams per square centimeter.

2. The posture enhancement device of claim 1, wherein the posterior portion is configured to be aligned with a shoulder blade, and the anterior portion is configured to be aligned with a collar bone, such that the posture signaling panel is configured to signal the human body to center and become aligned.

3. The posture enhancement device of claim 1, wherein the posture signaling panel is slidably coupled to the first arm strap and the second arm strap.

4. The posture enhancement device of claim 1, wherein the posture signaling panel is operable to stimulate intercostal muscles of the human body to enhance breathing.

5. The posture enhancement device of claim 1, wherein the first pressure level is greater than 30 grams per square centimeter.

6. The posture enhancement device of claim 1, wherein the torso strap comprises a first material, and the posture signaling panel comprises a second material, and
   wherein the first material has a first elasticity, and the second material has a second elasticity, wherein the first elasticity is different than the second elasticity.

7. The posture enhancement device of claim 1, wherein the posture signaling panel is configured to induce a collar bone to lift and to center the head and neck over the human body.

8. The posture enhancement device of claim 1, wherein the posture signaling panel is operable to stimulate muscles in the shoulder and back to release the shoulder joint such that a humerus bone hangs freely from the shoulder joint.

9. The posture enhancement device of claim 1, wherein the posture enhancement device does not include any braces or physically hold any part of the human body in place or in any orientation.

10. The posture enhancement device of claim 1, further comprising:
    a connection point adjustable so that the first arm strap adjusts to various angles relative to the torso strap and the posture signaling panel.

11. A method of making a posture device, the method comprising:
    attaching a torso strap to a coupling device configured to hold the posture device to a human body at a first force;
    directly coupling a first end of a first arm strap and a second arm strap to the torso strap, wherein open spaces are left between the first arm strap and the torso strap and between the second arm strap and the torso strap;
    attaching an anterior portion and a posterior portion of a posture signaling panel to the torso strap, wherein open spaces are left between the posture signaling panel and the first arm strap and between the posture signaling panel and the second arm strap; and attaching a first side portion and a second side portion of the posture signaling panel to the first arm strap and the second arm strap respectively, wherein the posture signaling panel is configured to provide a second force to the human body to correct posture of the human body.

12. The method of claim 11, wherein the first force is greater than 30 grams per square centimeter and the second force is in a range of 5 to 30 grams per square centimeter.

13. The method of claim 11, wherein the posture signaling panel, the first arm strap, and the second arm strap do not include any braces or physically hold any part of the human body in place or in any orientation.

* * * * *